United States Patent [19]

Inoue et al.

[11] Patent Number: 4,787,740

[45] Date of Patent: Nov. 29, 1988

[54] APPARATUS AND METHOD FOR DETERMINING CRYSTAL ORIENTATION

[75] Inventors: Yasuo Inoue; Tadashi Nishimura; Kazuyuki Sugahara; Shigeru Kusunoki, all of Hyogo, Japan

[73] Assignee: Mitsubishi Denki Kabushiki Kaisha, Tokyo, Japan

[21] Appl. No.: 11,329

[22] Filed: Feb. 5, 1987

[30] Foreign Application Priority Data

Feb. 8, 1986 [JP] Japan .................. 61-26166

[51] Int. Cl.⁴ .......................... G01N 21/00
[52] U.S. Cl. .................... 356/31; 356/301
[58] Field of Search ............ 356/31, 30, 369, 364, 356/301

[56] References Cited

PUBLICATIONS

"A Simple Fourier Photopolarimeter with Rotating Polarizer an Analyzer for Measuring", Jones and Mueller Matrices.

*Appl. Phys. Lett.*, vol. 44, 1984, pp. 535–537, J. B. Hopkins et al.

*Primary Examiner*—R. A. Rosenberger
*Assistant Examiner*—Crystal Cooper
*Attorney, Agent, or Firm*—Lowe, Price, Leblanc, Becker & Shur

[57] ABSTRACT

An apparatus for determining crystal orientation comprises: a polarizer for polarizing an incident light beam; a polarization analyzer for selecting light having a selected polarization direction in Raman scattered light; and a synchronizer for enabling synchronous rotations of the polarizer and the polarization analyzer.

8 Claims, 3 Drawing Sheets

4,787,740

APPARATUS AND METHOD FOR DETERMINING CRYSTAL ORIENTATION

BACKGROUND OF THE INVENTION

1. Field of the Invention

The present invention relates to an apparatus and a method for determining crystal orientation, and more particularly to improvement in an apparatus and a method which utilize polarization selective Raman microprobe spectroscopy.

2. Description of the Prior Art

Raman microprobe determination of crystal orientation is described, e.g., in *Appl. Phys. Lett.*, vol. 44, 1984, pp. 535–537 by J. B. Hopkins et al.

The Raman scattering intensity I is expressed by the following formula:

$$I \propto (\vec{e_1} R^j \vec{e_2})^2 \quad (1)$$

where $\vec{e_1}$ and $\vec{e_2}$ the polarization vectors of the incident light and the scattered light respectively, and $R^j$ represents a Raman tensor.

Referring to FIG. 1, there is shown a conceptional perspective view illustrating the geometrical relation between the polarizations of incident light and scattered light. Incident light 1 having a polarization direction 2 is focused on a specimen 5 of silicon or the like. The intensity I of scattered light 3 having a component 4 of the polarization direction is measured through a polarization analyzer. A series of the intensity measurements represents the polarization characteristic which reflects the crystal orientation. The geometrical relation between the incident light beam 1 and the crystal axes <100> can be determined by fitting a measured intensity profile of the scattered light 3 taken as a function of the polarization angles to that derived from the formula (1) as to known crystal orientation.

Referring to FIG. 2, there is shown a block diagram of a prior art apparatus for determining crystal orientation. A laser beam 12 emitted from a laser source 11 is passed through a spectroscopic filter 13 and the natural light is eliminated. The polarization direction of the filtered beam 12 is controlled by a polarizer 14 and then the beam 12 is expanded by a beam expander 15. The expanded beam is deflected by a half mirror 16 and focused by a lens 17 on a specimen 5 of which crystal orientation is to be determined. At this time, light having spectroscopic energies different from that of the original laser beam 12 is emitted as Raman scattered light from the specimen 5. The Raman scattered light 19 is collected by the lens 17 and deflected by a mirror 20 toward a polarization analyzer 21 in which light having a predetermined polarization direction is selected. The selected Raman scattered light is passed through a depolarizer 22 and focused by a lens 23 on a slit of a spectrometer 24. Spectra separated in the spectrometer 24 are detected by a photodetector 25, and then obtained data are processed by a computer 26 thereby to determine crystal orientation.

During measurements with this apparatus, the polarization direction of only either one of the incident beam and the scattered beam is systematically changed by correspondingly rotating only either one of the polarizer 14 and the polarization analyzer 21. Thus, it takes a long time to analyze the data, and the crystal orientation can not be determined three-dimensionally by one series of the measurements.

SUMMARY OF THE INVENTION

In view of the prior art, it is a major object of the present invention to provide an apparatus and a method with which it takes a shorter time to analyze the data and the crystal orientation can be determined three-dimensionally by only one series of the measurements.

According to an aspect of the present invention, an apparatus for determining crystal orientation comprises: a light source for emitting a incident light beam; a spectroscopic filter through which the beam is passed; a polarizer for polarizing the beam; a lens for focusing the beam on a specimen to cause Raman scattered light; a polarization analyzer for selecting light having a selected polarization direction in the scattered light; means for enabling synchronous rotations of the polarizer and the polarization analyzer; a depolarizer for depolarizing the scattered light; a spectrometer for separating the scattered light into its spectral components; a lens for focusing the scattered light on the spectrometer; a photodetector for detecting the spectral components and obtaining data; and a computer for processing the data to determine the crystal orientation.

According to another aspect of the present invention, a method for determining crystal orientation comprises the steps of: passing an incident light beam through a spectroscopic filter; polarizing the beam by a polarizer; focusing the beam on a specimen to cause Raman scattered light; selecting light having a selected polarizaiton direction in the scattered light by a polarization analyzer; synchronizing rotations of the polarizer and the polarizaiton analyzer; depolarizing the selected light; separating the depolarized light into its spectral components; detecting the spectral components and obtaining data; and processing the data to determine the crystal orientation by a computer.

These objects and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
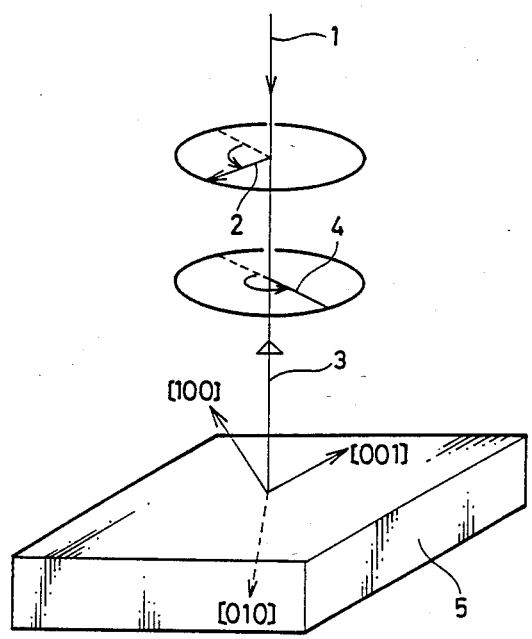
FIG. 1 is a conceptional perspective view illustrating the relation between the polarizations of incident light and Raman scattered light.
Figure 2:
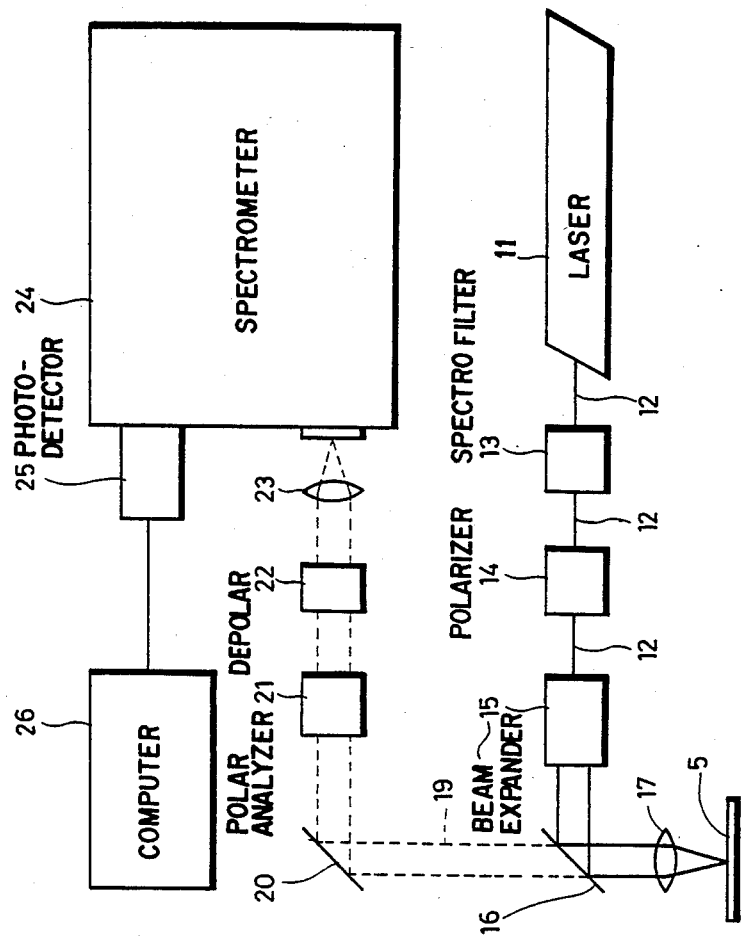
FIG. 2 is a block diagram of a prior art apparatus for determing crystal orientation.
Figure 3:
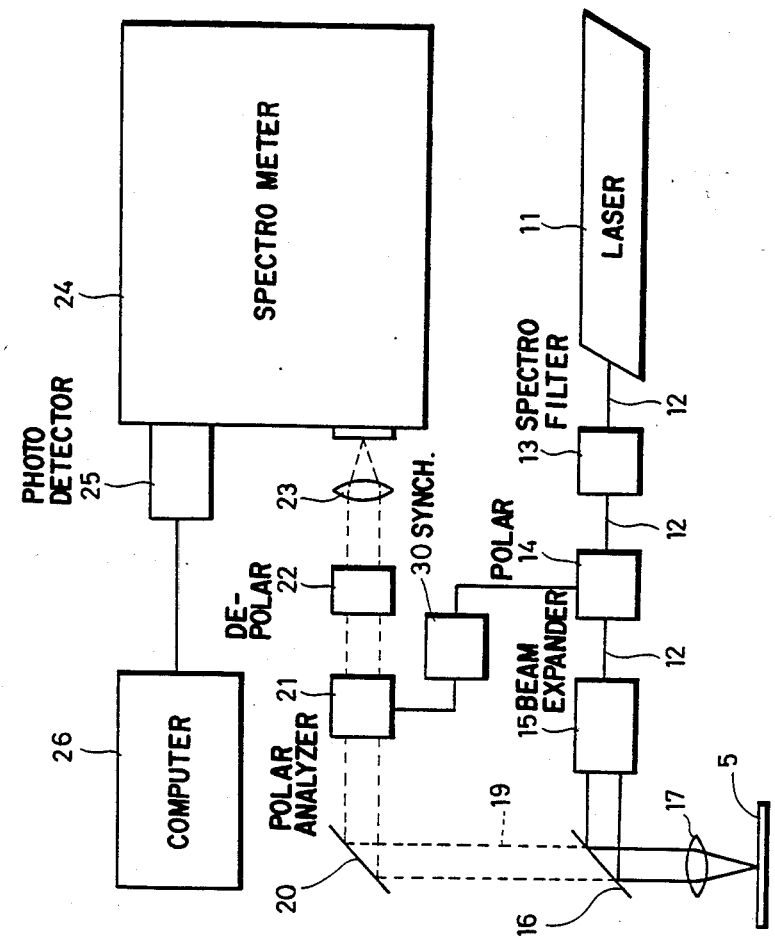
FIG. 3 is a block diagram of an apparatus according to an embodiment of the present invention.

Referring to FIG. 3, there is shown a block diagram of an apparatus according to an embodiment of the present invention. It is noted that the same reference characters are used in this figure as in FIG. 2 for corresponding blocks. This apparatus is similar to that of FIG. 2 but is provided with a synchronizer 30 which enables synchronous rotations of the polarizer 14 and the polarization analyzer 21.

Figure 4:
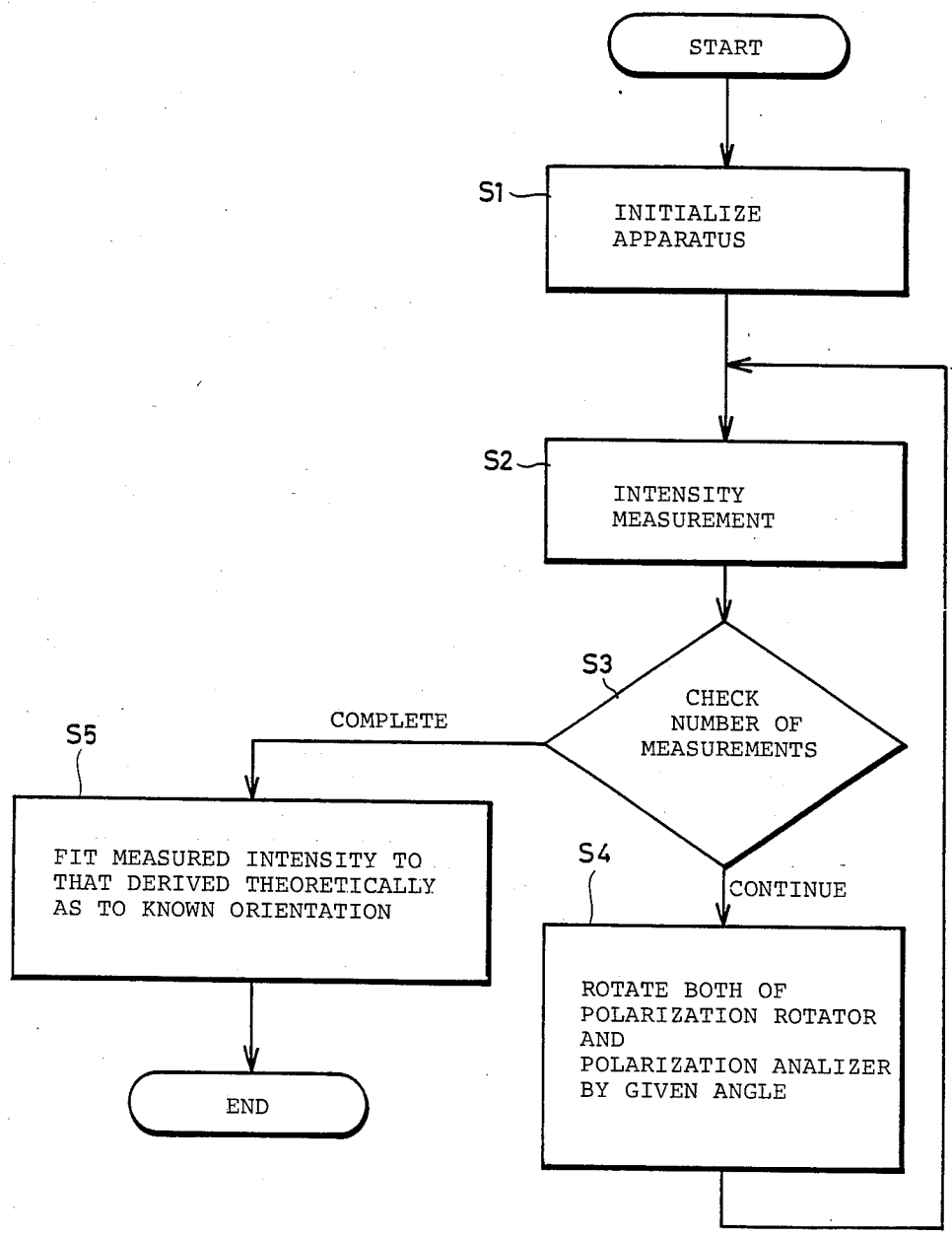
FIG. 4 is a flow chart of crystal orientation determination with the apparatus of FIG. 3.

Referring to FIG. 4, there is shown a flow chart of crystal orientation determination with the apparatus of FIG. 3. At the step S1, the apparatus is initialized to set both of the polarizer 14 and the polarization analyzer 21 at the initial reference angle of their rotation. At the step S2, the intensity of the Raman scattered light is measured. At the step S3, the number of the measurements is checked whether it has run up to a predetermined number. If the predetermined number of measurements have completed, the series of measured intensities are fitted by the least square method to that derived from the formula (1) as to known crystal orientation, as indicated at the step S5. If the predetermined number of measurements have not yet completed, the polarizer 14 and the polarization analyzer 21 both are synchronously rotated in phase by a predetermined angle, as indicated at the step S4. Thereafter, the steps 2 and 3 are repeated.

During one series of the intensity measurements, the polarizer 14 and the polarization analyzer 21 both are synchronously rotated in phase and at 5°-6° intervals from 0° to 180°. In other words, the relation of $\vec{e_1} = \vec{e_2}$ is maintained in the formula (1) during the series of the measurements. This means decrease in the number of parameters in the formula (1). Therefore, the time required for fitting the series of the measured intensities to that derived from the formula (1) becomes shorter, and further the crystal orientation can be determined three-demensionally by only one series of the measurements.

Although the relation of $\vec{e_1} = \vec{e_2}$ is maintained in the above described embodiment, it will be understood that the similar effect is brought if the angle between $\vec{e_1}$ and $\vec{e_2}$ is maintained constant during the series of the measurements.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for determining crystal orientation, comprising:
    a light source for emitting an incident light beam;
    a spectroscopic filter through which the beam is passed;
    a polarizer for polarizing the beam;
    a lens for focusing the beam on a specimen in order to cause Raman scattered light;
    a polarization analyzer for selecting light having a selected polarization direction in said scattered light;
    means for enabling synchronous rotation of said polarizer and said polarization analyzer in phase with and at the same angular speed as each other;
    a depolarizer for depolarizing said scattered light;
    a spectrometer for separating said scattered light into spectral components thereof;
    a lens for focusing said scattered light on said spectrometer;
    a photodetector for detecting said spectral components of said scattered light and obtaining data; and
    a computer for processing said data to determine said crystal orientation.

2. An apparatus in accordance with claim 1, wherein said light source is a laser for emitting a laser beam.

3. An apparatus in accordance with claim 2 further comprising a beam expander for expanding the laser beam.

4. A method for determining crystal orientation, comprising the steps of:
    passing an incident light beam through a spectroscopic filter;
    polarizing said incident light beam by a polarizer;
    focusing said beam on a specimen in order to cause Raman scattered light;
    selecting light having a selected polarization direction in said scattered light by a polarization analyzer;
    synchronizing rotation of said polarizer and said polarization analyzer to have the same angular speed and be in phase with each other;
    depolarizing said selected light;
    separating said depolarized light into spectral components thereof;
    detecting said spectral components and obtaining data; and
    processing said data by a computer to determine said crystal orientation.

5. An apparatus in accordance with claim 1 wherein said incident light beam and said Raman scattered light have different wavelengths.

6. An apparatus in accordance with claim 4 wherein said incident light beam and said Raman scattered light have different wavelengths.

7. An apparatus for determining crystal orientation, comprising:
    a light source for emitting an incident light beam at a first wavelength;
    a spectroscopic filter through which the beam is passed;
    a polarizer for polarizing the beam;
    a lens for focusing the beam on a specimen to cause Raman scattered light at a second wavelength different from the first wavelength;
    a polarization analyzer for selecting light having a selected polarization direction in said scattered light;
    means for enabling synchronous rotation of said polarizer and said polarization analyzer;
    a depolarizer for depolarizing said scattered light;
    a spectrometer for separating said scattered light into spectral components thereof;
    a lens for focusing said scattered light on said spectrometer;
    a photodetector for detecting said spectral components of said scattered light and obtaining data; and
    a computer for processing said data to determine said crystal orientation.

8. A method for determing crystal orientation, comprising the steps of:
    passing an incident light beam of a first wavelength through a spectroscopic filter;
    polarizing said incident light beam by a polarizer;
    focusing said beam on a specimen in order to cause Raman scattered light of a second wavelength different from the first wavelength;
    selecting light having a selected polarization direction in said scattered light by a polarization analyzer;
    synchronizing rotation of said polarizer and said polarization analyzer to each other;
    depolarizing said selected light;
    separating said depolarized light into spectral components thereof;
    detecting said spectral components and obtaining data; and
    processing said data by a computer to determine said crystal orientation.

* * * * *